US008353915B2

(12) United States Patent
Helenbolt et al.

(10) Patent No.: US 8,353,915 B2
(45) Date of Patent: Jan. 15, 2013

(54) AMZ TIBIAL TUBEROSITY TRANSFER SYSTEM

(75) Inventors: Kenneth T. Helenbolt, Naples, FL (US); David C. Koogle, Jr., Bonita Springs, FL (US); Robert K. Sluss, Naples, FL (US); William C. Carapezza, Land O Lakes, FL (US)

(73) Assignee: Arthrex, Inc., Naples, FL (US)

( * ) Notice: Subject to any disclaimer, the term of this patent is extended or adjusted under 35 U.S.C. 154(b) by 555 days.

(21) Appl. No.: 12/487,578

(22) Filed: Jun. 18, 2009

(65) Prior Publication Data

US 2009/0318924 A1 Dec. 24, 2009

Related U.S. Application Data

(60) Provisional application No. 61/074,113, filed on Jun. 19, 2008.

(51) Int. Cl.
*A61B 17/56* (2006.01)

(52) U.S. Cl. .............................. 606/87; 606/102; 606/88

(58) Field of Classification Search .............. 606/86 R, 606/87, 88, 89, 90, 96, 102, 104
See application file for complete search history.

(56) References Cited

U.S. PATENT DOCUMENTS

| 2002/0165552 | A1 | 11/2002 | Duffner | |
|---|---|---|---|---|
| 2004/0158255 | A1* | 8/2004 | Justin et al. | 606/87 |
| 2005/0075641 | A1 | 4/2005 | Singhatat et al. | |
| 2008/0154267 | A1* | 6/2008 | Merchant et al. | 606/87 |
| 2010/0076564 | A1* | 3/2010 | Schilling et al. | 623/20.14 |

FOREIGN PATENT DOCUMENTS

| WO | WO 2006/086476 A2 | 8/2006 |
|---|---|---|
| WO | WO 2008/005271 A2 | 1/2008 |

OTHER PUBLICATIONS

Farr, Distal Realignment for Recurrent Patellar Instability, 2001, WB Saunders, Operative Techniques in Sports Medicine vol. 9 No. 3 July, 176-182.*
Bicos et al., Indication and Technique of Distal Tibial Tubercle Anteromedialization, 2007, Elsevier, Operative Techniques in Orthopaedics 17, 223-233.*
Davis et al., Mechanical Comparison of Fixation Techniques for the Tibial Tubercle Osteotomy, 2000, LWW, CORR #380, 241-249.*
Mayo, Tibial Tuberosity Advancement, 2006, 1-12.*
Farr et al., Tibial Tuberosity Osteotomies, 2010, Elsevier, Operative Techniques in Sports Medicine 18, 107-114.*
P.R. Beck et al., "Trochlear Contact Pressures After Anteromedialization of the Tibial Tubercle," The American Journal of Sports Medicine, vol. 33, No. 11, pp. 1710-1715, 2005.
P.R. Beck et al., "Patellofemoral Contact Pressures Following Anteromedialization of the Tibial Tubercle," Rush University Medical Center, Thesis Day, May 28, 2004.

* cited by examiner

*Primary Examiner* — Thomas Barrett
*Assistant Examiner* — Michael T. Schaper
(74) *Attorney, Agent, or Firm* — Dickstein Shapiro LLP

(57) ABSTRACT

An AMZ tibial tuberosity transfer system and method of treatment of patellofemoral joints. The AMZ system includes 1) a retractor with a better conformation to anatomy and more curve (not just a bend), and also with a larger radius on the front of the retractor to allow for easier insertion; 2) a cutting block that can fully accept a collared pin; 3) a rod preferably formed of stainless steel; 4) a tuberosity pin guide; 5) an exit indicator that engages tightly the cutting block so there is no slope on exit indication; and 6) a horizontal bar provided with markings to measure the medial shift.

7 Claims, 10 Drawing Sheets

AMZ TIBIAL TUBEROSITY TRANSFER SYSTEM

CROSS-REFERENCE TO RELATED APPLICATIONS

This application claims the benefit of U.S. Provisional Application No. 61/074,113, filed Jun. 19, 2008, the entire disclosure of which is incorporated by reference herein.

FIELD OF THE INVENTION

The present invention relates to treatment of patellofemoral joints and, more particularly, to improved instrumentation and methods of quantifying the shift in the anterior and medial direction of the tibial tuberosity when performing the anteromedialization (AMZ) procedure.

BACKGROUND OF THE INVENTION

The patellofemoral joint presents a complex challenge to surgeons. Patellofemoral dysfunction (instability or pain) is often a result of an abnormal, lateral position of the tibial tuberosity. One method of treating patellar problems is tibial tuberosity osteotomy, wherein the tuberosity is moved to allow treatment of patellar pain and/or instability.

The assumption that the original tuberosity position is abnormal or suboptimal for distributing force is the reason for moving the tuberosity to a new position. Anteromedialization (AMZ) of the tuberosity is typically achieved by an oblique cut between the sagittal and coronal planes of the tuberosity. The obliquity can be altered to achieve the same degree of elevation with various degrees of medialization (the steeper the cut, the less the medialization). The desired slope of the osteotomy is determined preoperatively. The AMZ procedure begins by lateral release of subcutaneous tissues along the patellar tendon. A guide is used to position the tuberosity pin perpendicular to the posterior wall of the tibia. A horizontal guide, with a predetermined angle, is placed over the tuberosity pin. A cutting block is attached to the horizontal guide on the medial aspect of the tuberosity. The horizontal guide and cutting guide are adjusted so that the position of the cutting block is medial to the tuberosity in a posteromedial to anteromedial orientation as it travels distally. The obliquity of the jig will allow the distal cut of the tuberosity to exit laterally, fully freeing the tuberosity.

Two breakaway pins are inserted into the tibia to help secure the cutting block. The angle of the slope is visualized as the slope selector outrigger-aiming device is temporarily applied to the block. The tip of the slope selector is placed posteriorly on the lateral face of the tibia (this predetermines where the osteotomy will exit).

Once the slope and planned cut exit have been determined, the cutting block is attached to the tibia with fixation pins (placed through holes in the cutting block) into drill holes in the tibia. A custom retractor is placed posterior to the tibia to protect deep neurovascular structures. An oblique cut is made from the proximal extent of the posterior cut to the lateral proximal attachment of the patellar tendon to the tuberosity. Once the tuberosity is fully released, and after the desired (final) tuberosity position is achieved, the newly-repositioned tuberosity is typically fixed by employing two interfragmentary screws.

Improved instrumentation and methods of quantifying the shift in the anterior and medial direction of the tibial tuberosity when performing the AMZ procedure are needed.

SUMMARY OF THE INVENTION

The present invention provides an improved tibial tuberosity transfer (T3) system and methods of quantifying the shift in the anterior and medial direction of the tibial tuberosity when performing the AMZ procedure.

The AMZ instruments of the present invention have an improved design that accurately quantifies the shift in the anterior and medial direction of the tibial tuberosity. The AMZ system of the present invention comprises: 1) a retractor with a better conformation to anatomy and more curve (not just a bend), and also with a larger radius on the front of the retractor to allow for easier insertion; 2) a cutting block that that can fully accept a collared pin; 3) a rod preferably formed of stainless steel; 4) a tuberosity pin guide; 5) an exit indicator that engages tightly the cutting block so there is no slope on exit indication; and 6) a horizontal bar provided with markings to measure the medial shift.

Other features and advantages of the present invention will become apparent from the following description of the invention, which refers to the accompanying drawings.

DETAILED DESCRIPTION OF THE PREFERRED EMBODIMENTS

In the following detailed description, reference is made to various specific embodiments in which the invention may be practiced. These embodiments are described with sufficient detail to enable those skilled in the art to practice the invention, and it is to be understood that other embodiments may be employed, and that structural and logical changes may be made without departing from the spirit or scope of the present invention.

The present invention provides an improved tibial tuberosity transfer system and methods of quantifying the shift in the anterior and medial direction of the tibial tuberosity when performing the AMZ procedure. The AMZ system of the present invention comprises various instruments having improved design that confer improved quantification of the degree in the shift of the tibial tuberosity and improved realignment of the tuberosity which is precisely guided. The AMZ system of the present invention also confers improved patellofemoral procedures with reduced risks of knee infections, arthrofibrosis, complex regional pain syndrome, malunion, nonunion, failure of fixation, and fracture.

Referring now to the drawings, where like elements are designated by like reference numerals, FIGS. 1-7 illustrate various views of an AMZ system 100 of the present invention that comprises a retractor 10 that has a better conformation to the anatomy of tibial tuberosity 91 of tibia 90 and a curve (not just a bend) compared to the known retractors for AMZ procedures. Retractor 10 (FIGS. 1, 4 and 7) is also configured to have a larger radius on the front of the retractor to allow for easier insertion. If desired, the gradation marks of the retractor 10 may be omitted. Retractor 10 may be provided as a reusable or disposable instrument.

Figure 1:
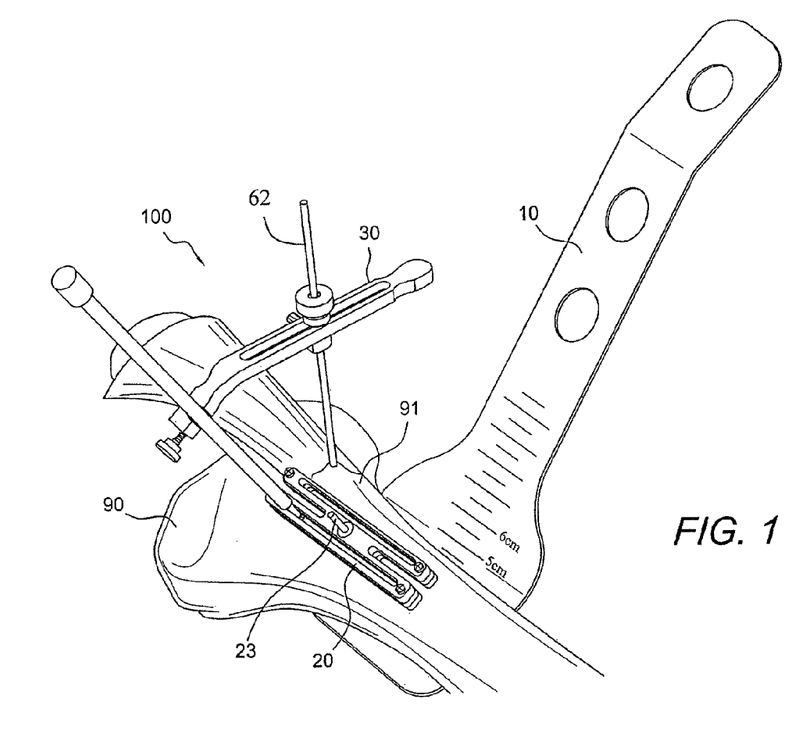
FIGS. 1-7 illustrate various perspective views (including partial and expanded views) of instruments that form the AMZ system of the present invention (comprising a cutting block, a retractor, a tuberosity pin guide, an exit indicator, a horizontal bar, and a rod)
Figures 2, 5:
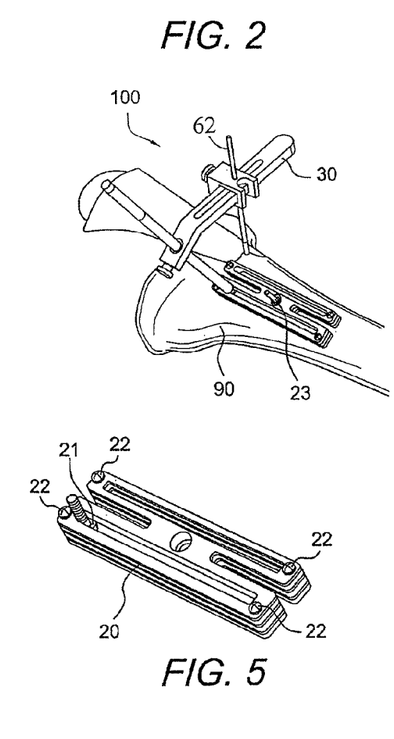
Figure 6:
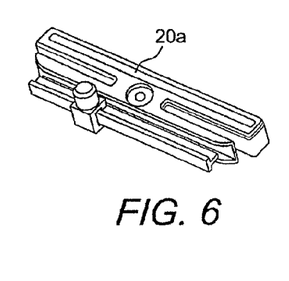

Cutting block or cutting guide 20 (shown in FIGS. 1-6) is preferably provided with a thread that can fully accept a collared pin. Cutting block 20 is illustrated, in an exemplary embodiment, as being a disposable, laminated block 20 (FIG. 5). Alternatively, and as shown in FIG. 6, the cutting block or guide may be a solid, milled block 20a that is reusable. If a disposable, laminated version is employed, the plates forming the cutting block may be laser cut and the cutting block may be configured to be screwed down or quickly riveted, to decrease costs. A captured slide screw 21 is also shown in FIG. 5. Fixation devices 22 (for example, pins or screws) are also shown in FIG. 5. These fixation devices may be screwed down or riveted to decrease costs. A hold-down pin 23 (a collared pin 23) is shown in FIGS. 2 and 5a to aid in the fixation of the cutting guide on tibia 90.

Figure 3:
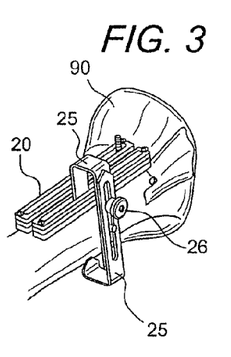
Figure 4:
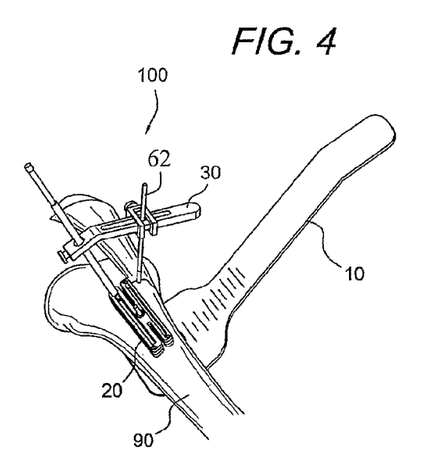
Figure 5A:
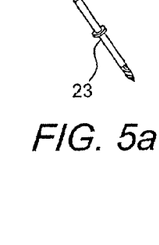

Cutting block 20 may be used in connection with blade exit tool 25 (blade exit indicator 25) shown in FIG. 3. Blade exit indicator 25 is provided with knob 26 which permits movement (sliding) of the indicator along the tibial surface of tibia 90 and precisely indicates the exact exit path (when the knob 26 is loose). If knob 26 is kept loose during use, the blade exit indicator 25 can slide along the bone surface and indicate the exact exit path of the blade (alternatively, the knob can be placed for a quick eyeball check). Exit indicator 25 fits tightly with the cutting block 20 (when the knob 26 is tight) so that there is no slope on exit indication.

Figure 7:
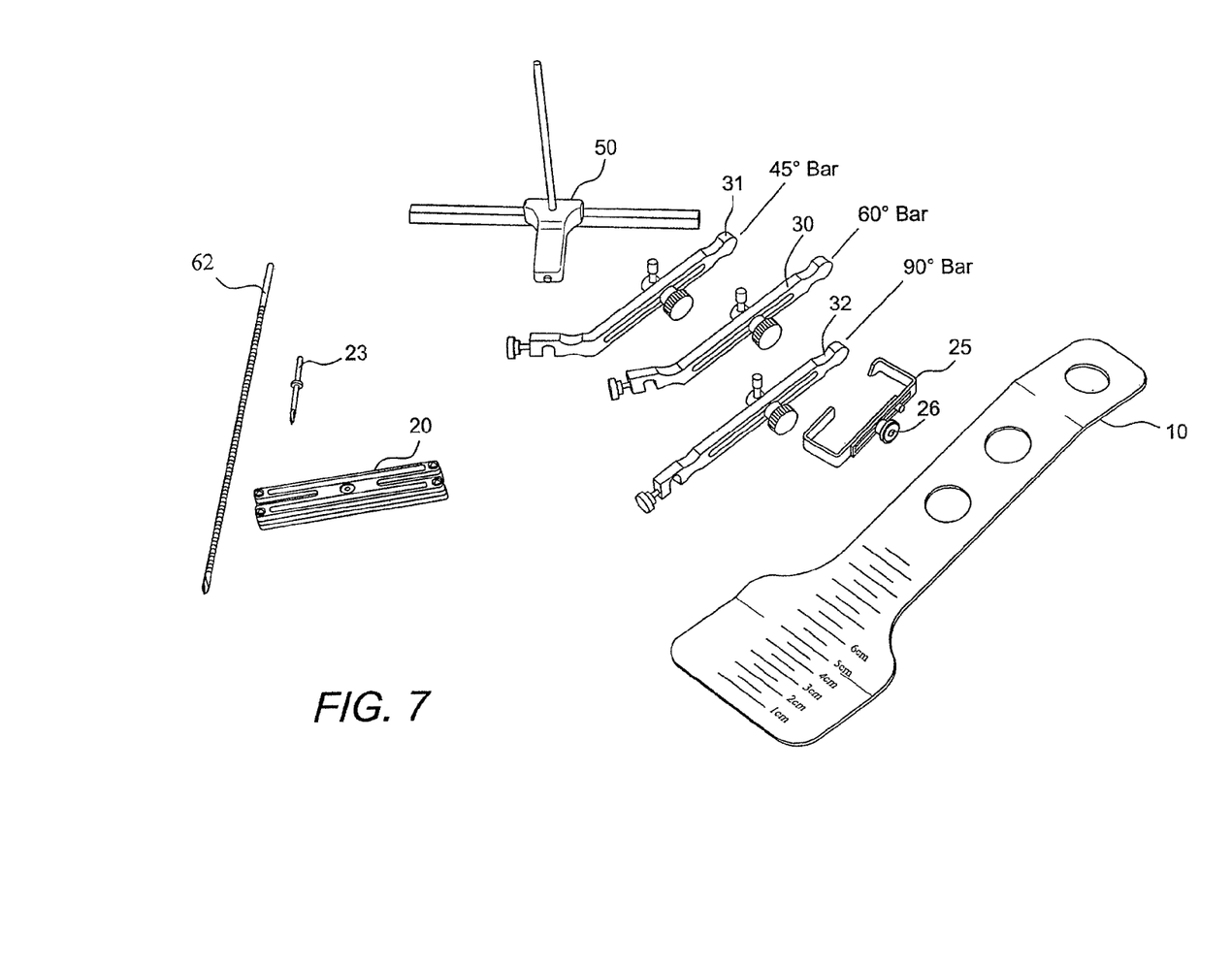

Horizontal guide 30 of the system 100 of the present invention may be provided in various configurations depending on the angle of the cut (i.e., a guide for each desired angle). For example, FIG. 7 illustrates horizontal guides 30, 31, 32 intended for 60 degrees, 45 degrees, and 90 degrees, respectively. Horizontal guide 30 is provided with markings for measuring the medial shift.

Tuberosity drill pin or rod 62 is preferably formed of stainless steel. A level/alignment indicator 50 is also provided. Drill pin 62, collared pin 23 and cutting block 20 may be disposable. Retractor 10, horizontal bar 30, 31, 32 with blade exit tool 25 and level/alignment indicator 50 may be reusable.

FIGS. 8-19 illustrate a sequence of steps of an AMZ procedure conducted by employing system 100 of the present invention including a plurality of surgical instruments that are designed to precisely quantify the shift in the anterior and medial direction of the tibial tuberosity when performing the AMZ procedure. The AMZ procedure detailed below is the surgical technique for tibial tuberosity osteotomy with anteromedialization (AMZ) for realignment of the extensor mechanism and unloading the patellofemoral joint (using the AMZ system 100 described above). As detailed below, the correct amount of anterior and medial tuberosity shift is achieved by determining the slope and selecting the corresponding T3 AMZ Horizontal Cutting Guide based upon the desired amount of correction.

Figure 8:
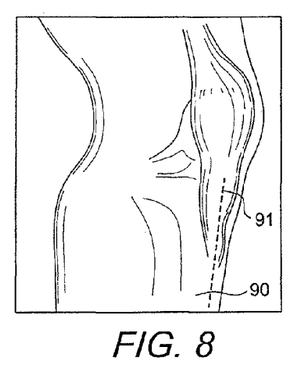
FIGS. 8-19 illustrate various steps of an AMZ procedure performed with instrumentation according to the present invention.

Reference is now made to FIG. 8. A longitudinal incision is made over the midline of the tibial tuberosity extending approximately 5 cm from the distal extent of the patellar tendon. The subcutaneous tissues are dissected from the underlying superficial fascia of the knee, exposing the distal insertion of the patellar tendon, the attachment to the tibial tuberosity and distally enough to allow for the Cutting Block 20.

Figure 9:
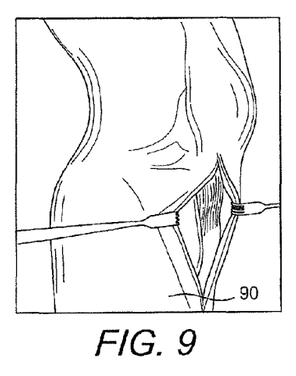

As shown in FIG. 9, incisions are made longitudinally medial and lateral to the patellar tendon to allow for anteriorization. The blood vessels and additional structures behind the tibia are protected with a retractor. The anterior compartment musculature is elevated from the lateral wall of the tibia 90, beginning distal to Gerdy's tuberosity, to gain access to the posterolateral tibia.

Figure 10:
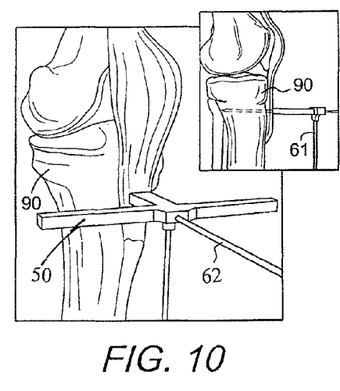

The alignment indicator 50 is positioned using the femoral condyles and ankle as reference points, on to the tuberosity below the level of Gerdy's tuberosity (FIG. 10). The Tuberosity Pin 62 is inserted into the tuberosity so it is oriented perpendicular to the posterior wall of the tibia 90 (FIG. 10). In most patients under anesthesia, the natural position of the limb is in external rotation, so an assistant may need to aid in the positioning of the limb.

Figure 11:
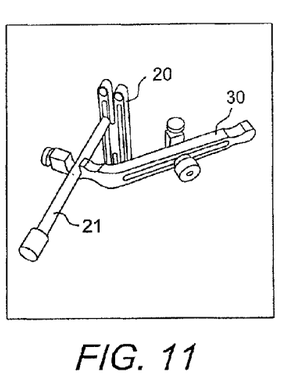

FIG. 11 illustrates the assembling of the cutting guide by first attaching the T3 AMZ Cutting Block Post 21 into the Cutting Block 20. The Cutting Block Post 21 is secured into the post slot of the appropriate T3 AMZ Horizontal Guide 30. The screw is loosely tightened to hold the Cutting Block Post 21 in place.

Figure 12:
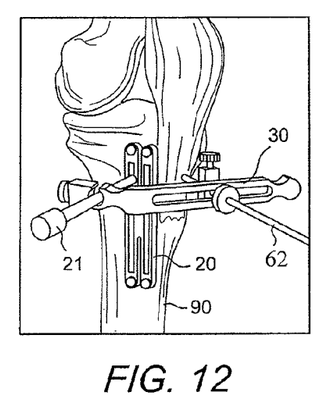

Reference is now made to FIG. 12. The Horizontal Guide 30 is slid over the Tuberosity Pin 62; its locking nut and screw are temporarily tightened to hold the Cutting Block 20 in place on the medial aspect of the tuberosity.

Figure 13:
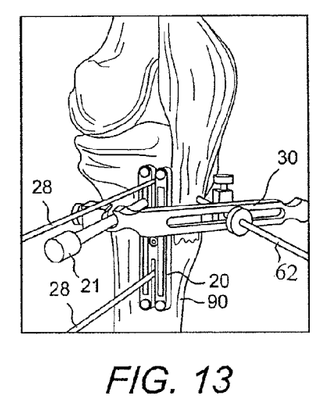

The position of the Cutting Block 20 is adjusted so that the Block is positioned medial to the tuberosity in a posteromedial to anteromedial orientation as it travels distally (FIG. 13). The Cutting Block Post 21 and all three locking screws on the Horizontal Guide 30 are tightened to hold the Cutting Block 20 securely in place. Two T3 AMZ Breakaway Pins 28 are inserted into the middle slots of the Cutting Block 20, taking care not to penetrate the posterolateral cortex of the tibia.

Figure 14:
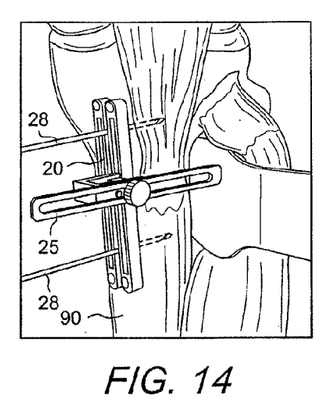

The Horizontal Guide 30 is released from the Cutting Block Post 21 and the Cutting Block Post 21 is removed from the Cutting Block 20, leaving the Cutting Block 20 in place (FIG. 14). The Horizontal Guide 30 and the Tuberosity Pin 62 are removed. The T3 AMZ Saw Blade Exit Indicator 25 in the cutting slot of the Cutting Block 20 is used to visualize on the posterolateral tibial cortex where the saw blade will exit. The position of the Cutting Block 20 is readjusted, either superiorly or inferiorly.

Figure 15:
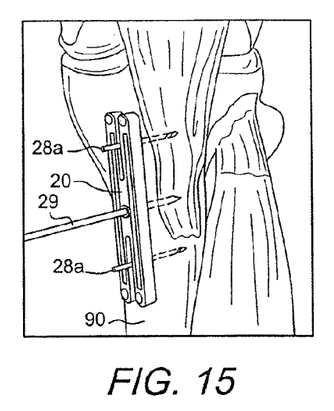

As shown in FIG. 15, the excess Breakaway Pins are snapped off, leaving Pins 28a approximately 1 cm above the Cutting Block 20, and the Collared Breakaway Pin 29 is inserted into the center hole of the Cutting Block 20. Any excess Collared Breakaway Pin is also snapped off, so it will not obstruct the sagittal saw.

Figure 16:
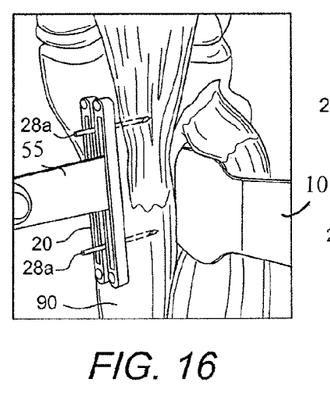

With the Soft Tissue Retractor 10 in place, the tuberosity 91 is cut through using a sagittal saw 55 along the top slot of the Cutting Block 20 (FIG. 16). The saw blade 55 is moved superior and inferior. Care may be taken in avoiding completely detaching the tuberosity distally and leaving a small bridge of periosteum.

Figure 17:
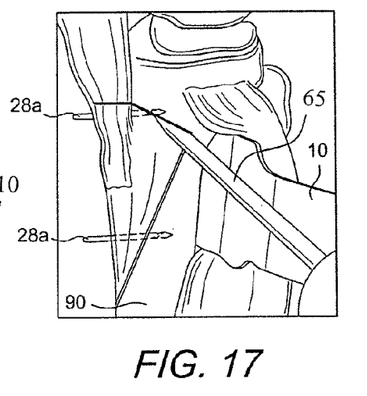

As shown in FIG. 17, the Collared Breakaway Pin 20 and the Cutting Block 20 are removed, leaving Pins 28a in place. The proximal osteotomy is finished medially and laterally at the level of the insertion of the patellar tendon using a small osteotome 65 and a mallet.

Figure 18:
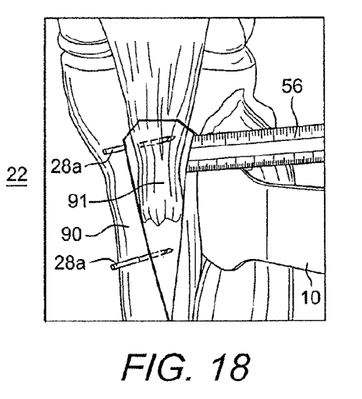

Referring now to FIG. 18, using a ruler 56, the amount of anterior and medial shift necessary to correct the patellar malalignment from preoperative planning is measured. Alternatively, the graduated markings on the Pins 28a and the angle of the horizontal guide 30 can be used to determine the amount of anterior and medial shift.

Figure 19:
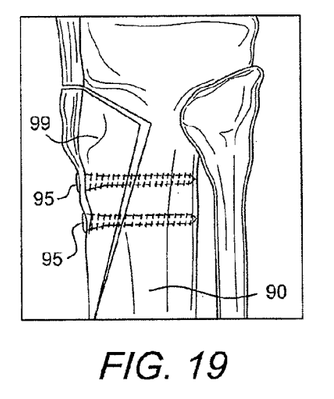
Figure 20:
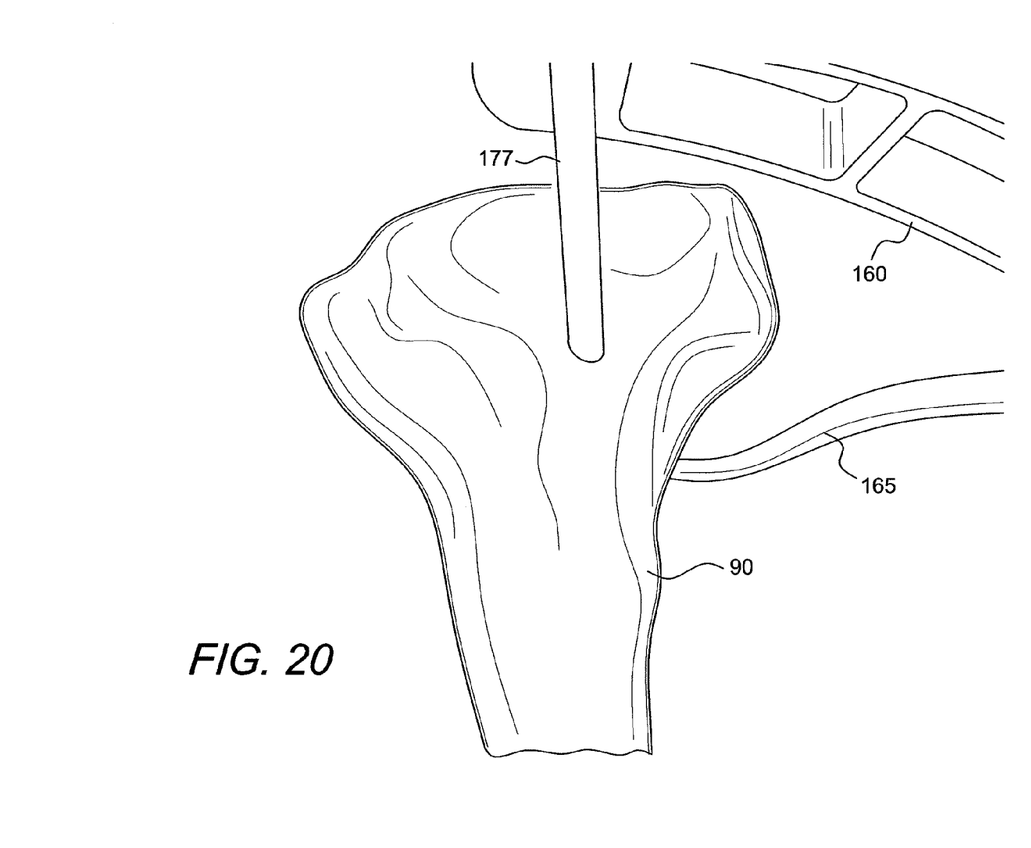
FIGS. 20-23 illustrate various views of a Constant Pin Guide that may be employed in lieu of the Tuberosity Pin Guide used in the sequence of steps of FIGS. 8-19.
Figure 21:
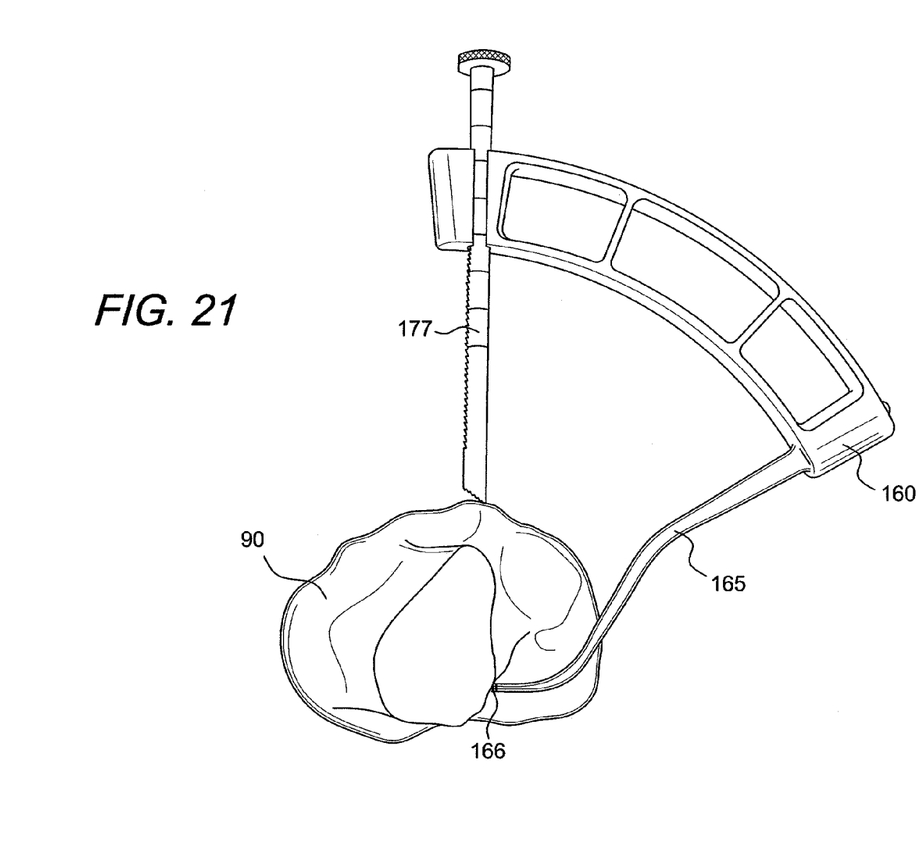
Figure 22:
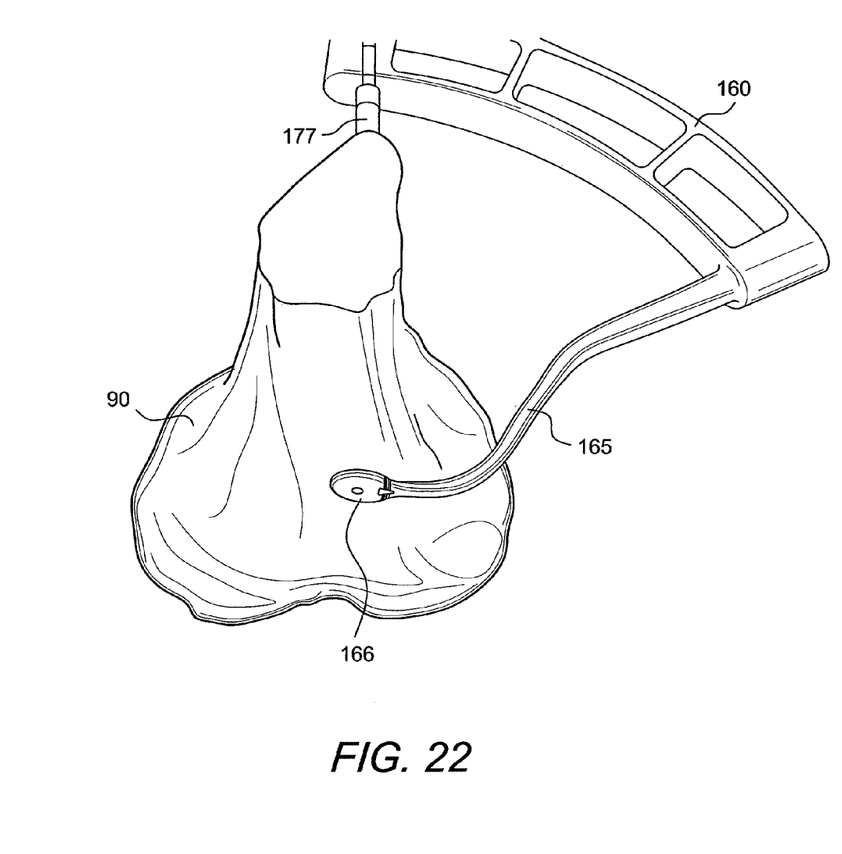
Figure 23:
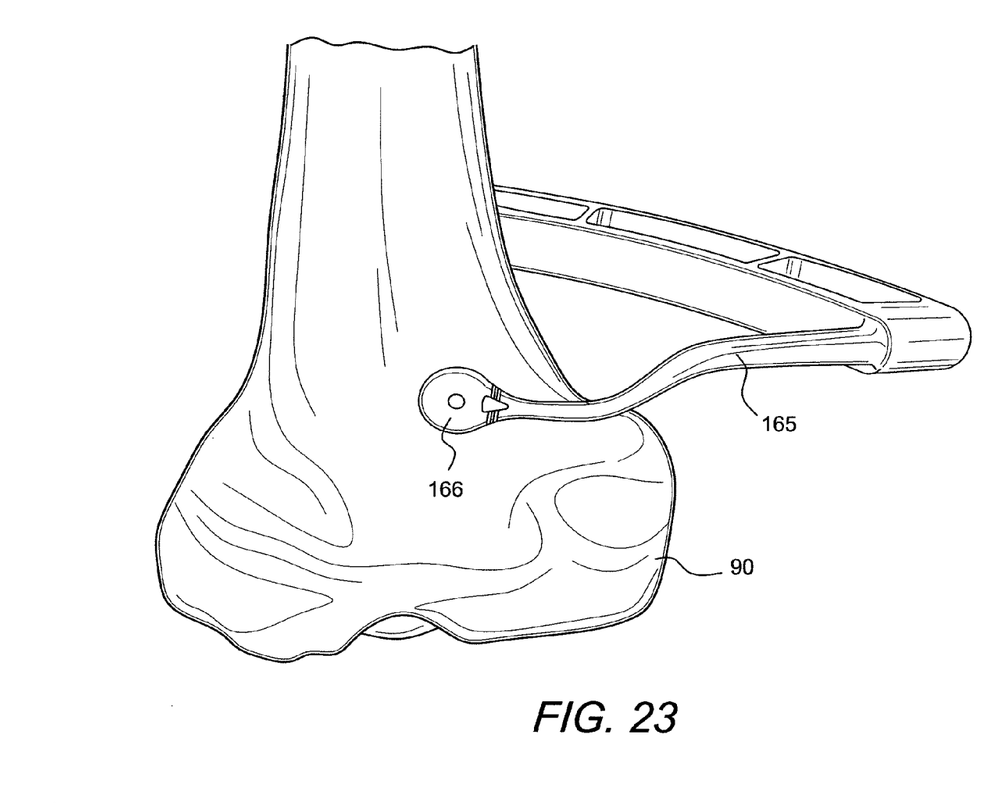

The tuberosity osteotomy is fixed by inserting two 4.5 mm cortical screws 95 in a lateral to medial angulation as they course posteriorly (FIG. 19). FIG. 19 illustrates a fully-seated AMZ tuberosity 99 by the procedure described above.

FIGS. 20-23 illustrate various views of a Constant Pin Guide 160 which is used to conduct the first step of the procedure detailed above and which would be an alternate to the Tuberosity Pin Guide 61 for placing the first pin in the tuberosity.

The Constant Pin Guide 160 shown in FIGS. 20-23 is provided with a flat distal tip 166 which is utilized to accurately place a guide pin into the tibial tuberosity 91 in a manner in which it is perpendicular to the posterior wall of the proximal tibia 90. The flat tip 166 of the guide 160 is placed on the posterior wall of the tibia 90 and the pin guide sleeve 177 of the guide 160 is lowered on to the tibial tuberosity 91 and tightened to allow the construct to be rigid. The tibial tuberosity pin (not shown) is advanced through the guide sleeve 177 of the guide 160 and into and through the tibial tuberosity 91. The flat distal tip 166 of the guide arm 165 which is positioned flat against the posterior wall of the proximal tibia 90 acts as a depth stop to prevent over penetration of the tuberosity pin.

The amount of medialization and/or anteriorization necessary is based upon the medial/lateral position of the tuberosity and the proximal/distal position of the patella. This is calculated based on the patient's TT-TG (tibial tuberosity-trochlear groove) distance and patellar height. The tuberosity can be simultaneously moved proximally or distally to address (normalize) patellar alta or infra. Normal TT-TG distance is approximately 15 mm based upon multiple studies. The slope of the osteotomy allows medialization to vary depending on the amount of optimal anteriorization. As shown in Table 1 below, all standard amounts of needed medialization can be typically achieved by using slopes of 45° or 60° and various amounts of anteriorization with the system 100 of the present invention.

TABLE 1

Medialization Achieved by Varying Slope and Anteriorization

| SLOPE | | | | | | | |
|---|---|---|---|---|---|---|---|
| 45° | Anterior Shift (mm) | 10.0 | 11.0 | 12.0 | 13.0 | 14.0 | 15.0 |
| | Medial Shift (mm) | 10.0 | 11.0 | 12.0 | 13.0 | 14.0 | 15.0 |
| 60° | Anterior Shift (mm) | 10.0 | 11.0 | 12.0 | 13.0 | 14.0 | 15.0 |
| | Medial Shift (mm) | 5.8 | 6.4 | 6.9 | 7.5 | 8.1 | 8.7 |

Although the present invention has been described in connection with preferred embodiments, many modifications and variations will become apparent to those skilled in the art. While preferred embodiments of the invention have been described and illustrated above, it should be understood that these are exemplary of the invention and are not to be considered as limiting. Accordingly, it is not intended that the present invention be limited to the illustrated embodiments, but only by the appended claims.

What is claimed as new and desired to be protected by Letters Patent of the United States is:

1. A method of quantifying shift in anterior and medial directions of a tuberosity of a tibia in an anteromedialization procedure, the method comprising the steps of:
   determining a slope of osteotomy;
   placing a retractor posterior to the tibia;
   quantifying a degree of shift in the anterior and medial directions of the tuberosity of the tibia to obtain a quantified deegree of shift; and
   selecting a horizontal bar corresponding to the quantified degree of shift; and
   conducting at least two cuts into the tuberosity with a system comprising: a cutting block secured medial to the tuberosity; a tuberosity drill pin; the horizontal bar configured to slidingly engage at least a portion of the tuberosity drill pin; and
   an exit indicator provided with a knob and configured to engage the cutting block and to slidingly move along a surface of the tuberosity and indicate an exit path of a cutting blade.

2. The method of claim 1, further comprising the steps of fully releasing the tuberosity and reattaching the tuberosity to the tibia.

3. The method of claim 1, further comprising the step of attaching the cutting block to the tibia by forming holes in the tibia and placing fixation devices through the cutting block and into the holes.

4. The method of claim 1, further comprising the step of selecting the horizontal bar based on an angle of each of the at least two cuts.

5. The method of claim 4, wherein the angle is one of a 45, 60 or 90 degree angle.

6. The method of claim 1, further comprising the step of securing the cutting block to the tuberosity by providing three pins.

7. The method of claim 6, wherein one of the pins locks the cutting block to the tuberosity and wherein the other two pins are designed to move relative to a longitudinal axis of the cutting block.

* * * * *